United States Patent [19]

Sklar

[11] Patent Number: 5,632,758

[45] Date of Patent: *May 27, 1997

[54] AUTOMATED SURGICAL INSTRUMENT

[75] Inventor: Martin J. Sklar, Needham, Mass.

[73] Assignee: Automated Medical Instruments, Inc., Needham, Mass.

[*] Notice: The term of this patent shall not extend beyond the expiration date of Pat. No. 5,350,355.

[21] Appl. No.: 270,821

[22] Filed: Jul. 5, 1994

Related U.S. Application Data

[63] Continuation of Ser. No. 837,352, Feb. 14, 1992, Pat. No. 5,350,355.

[51] Int. Cl.$^6$ .................................................. A61B 17/00
[52] U.S. Cl. .................................................. 606/170; 606/1
[58] Field of Search .......................... 128/4–6, 750–755; 606/1, 170–172, 174, 176, 205–211; 310/10–12, 20; 604/23

[56] References Cited

U.S. PATENT DOCUMENTS

| | | |
|---|---|---|
| 2,710,000 | 6/1955 | Cromer et al. . |
| 3,391,289 | 7/1968 | Danilewicz et al. . |
| 3,528,424 | 9/1970 | Ayres . |
| 3,817,251 | 6/1974 | Hasson . |
| 3,913,582 | 10/1975 | Sharon . |
| 3,926,192 | 12/1975 | Van Maren . |
| 3,945,597 | 3/1976 | Klein . |
| 4,016,881 | 4/1977 | Rioux et al. . |
| 4,143,652 | 3/1979 | Meier et al. . |
| 4,174,715 | 11/1979 | Hasson . |
| 4,342,951 | 8/1982 | Muller et al. . |
| 4,392,485 | 7/1983 | Hiltebrandt . |
| 4,418,692 | 12/1983 | Guay . |
| 4,473,074 | 9/1984 | Vassiliadis . |
| 4,491,435 | 1/1985 | Meier . |
| 4,503,842 | 3/1985 | Takayama . |
| 4,503,854 | 3/1985 | Jako . |
| 4,517,963 | 5/1985 | Michel . |
| 4,565,423 | 1/1986 | Ueda . |
| 4,573,452 | 3/1986 | Greenberg . |
| 4,600,938 | 7/1986 | Sluyter et al. . |
| 4,600,939 | 7/1986 | Sluyter et al. . |
| 4,600,940 | 7/1986 | Sluyter . |
| 4,611,888 | 9/1986 | Prenovitz et al. . |
| 4,639,772 | 1/1987 | Sluyter et al. . |
| 4,644,950 | 2/1987 | Valli . |
| 4,644,952 | 2/1987 | Patipa et al. . |
| 4,657,018 | 4/1987 | Hakky . |
| 4,700,702 | 10/1987 | Nilsson . |
| 4,708,125 | 11/1987 | Miketi et al. . |
| 4,784,137 | 11/1988 | Kulik et al. . |
| 4,791,934 | 12/1988 | Brunnett . |

(List continued on next page.)

FOREIGN PATENT DOCUMENTS

| | | |
|---|---|---|
| 1126119 | 6/1982 | Canada . |
| 0246086 | 11/1987 | European Pat. Off. . |
| 0449663A2 | 10/1991 | European Pat. Off. . |
| 2800607 | 10/1978 | Germany . |
| 143033 | 7/1980 | Germany . |

OTHER PUBLICATIONS

Foreman, Judy, "Endoscopy–The Real Cutting Edge", The Boston Globe, Health/Science Section, Oct. 28, 1991, pp. 25–26.

Primary Examiner—Michael Buiz
Assistant Examiner—William W. Lewis
Attorney, Agent, or Firm—Cesari & McKenna, LLP

[57] ABSTRACT

An automated surgical instrument provides a housing having a linear drive for moving a cannula toward and away from the housing. The housing may be supported stationarily while the cannula is driven to a predetermined location in the body through an incision. The end of the cannula includes a surgical tool or laparoscope to be positioned within an area undergoing an operation. Surgical tools can be actuated automatically by means of an actuator positioned in the housing and having a linkage extending through a lumen of the cannula to the tool. Both the actuator and the linear drive motor can be controlled by means of switches located on the housing or at another remote location.

29 Claims, 7 Drawing Sheets

U.S. PATENT DOCUMENTS

| | | |
|---|---|---|
| 4,846,155 | 7/1989 | Kimura . |
| 4,858,608 | 8/1989 | McQuilkin . |
| 4,863,133 | 9/1989 | Bonnell . |
| 4,905,668 | 3/1990 | Ohsawa . |
| 4,941,454 | 7/1990 | Wood et al. . |
| 4,944,738 | 7/1990 | Rodriguez . |
| 4,944,741 | 7/1990 | Hasson . |
| 4,959,710 | 9/1990 | Uehara et al. . |
| 4,977,886 | 12/1990 | Takehana et al. . |
| 4,982,725 | 1/1991 | Hibino et al. . |
| 5,002,557 | 3/1991 | Hasson . |
| 5,018,509 | 5/1991 | Suzuki et al. . |
| 5,019,121 | 5/1991 | Krauter . |
| 5,020,535 | 6/1991 | Parker et al. . |
| 5,026,387 | 6/1991 | Thomas . |
| 5,184,601 | 2/1993 | Putnam . |
| 5,350,355 | 9/1994 | Sklar . |

AUTOMATED SURGICAL INSTRUMENT

This application is a continuation of application Ser. No. 07/837,352 filed on Feb. 14, 1992, now U.S. Pat. No. 5,350,355.

FIELD OF THE INVENTION

This invention relates to an automated surgical instrument and a system for performing minimally invasive surgical procedures with such instruments.

BACKGROUND OF THE INVENTION

In recent years, the use of laparoscopic instruments to perform minimally invasive surgical procedures has become increasingly popular. In such procedures, a device termed a laparoscope, having an elongated substantially tubular member is inserted into the body of the patient through a relatively small incision in the skin. The distal end tube or "cannula" is positioned proximate an area inside the body upon which a surgical procedure is required. The distal end generally includes a lens and, typically, a light source to illuminate the interior of the body. The lens transmits received images from inside the body to a camera located, generally, outside of the body near a proximal end of the cannula. The camera may be interconnected to a video monitor so that a surgeon may view the operation area. Hence, the surgeon may view an interior portion of the body without the need of a large incision to open an area to external viewing.

Several additional laparoscopic instruments, also having elongated tubular cannuli, may be inserted through additional incisions in the skin to positions adjacent the laparoscope's distal end. These instruments may include a number of surgical tools including scissors, graspers and retractors capable of mechanical movement to perform desired surgical operations upon the area. The laparoscope allows the surgeon to view the progress of the instruments and, hence, guide the other laparoscopic instruments to perform the operation.

Conventional surgical procedures in which the surgeon performs the operation through an open incision, using hand tools such as scalpels and forceps, generally inflict significantly more trauma upon the patient and entail a more lengthy recovery time than for the relatively minor incisions necessitated by laparoscopic instruments. Thus, for many types of surgery, the use of laparoscopic instruments is largely preferred.

A disadvantage to the use of laparoscopic instruments, however, has been the need for a substantial number of operators in order to effectively employ the procedure. To date, most Laparoscopes and laparoscopic instruments have been designed strictly for hand-held manual operation. Some laparoscopes have utilized supports to aid in holding them stationarily, but insertion, retraction and readjustment of the cannula has been performed manually. Each instrument usually must be operated by a single staff member and that staff member must maintain the instrument in a proper location throughout the procedure by manually readjusting it as needed. For example, the camera may require frequent re-focusing and re-directing. In addition, instruments having tools that require manipulation must be operated by the user while the user simultaneously holds the laparoscope at an appropriate location which can tax the coordination of the user and quickly fatigue him or her.

The continual manipulation of instruments by hand, therefore, can seriously impede the efficiency of an operating staff, particularly during a long and difficult procedure.

In view of the disadvantages associated with the use of manually operated laparoscopic instruments, this invention has, as one object to provide a laparoscopic instrument that may be operated remotely by the user. This invention also enables more accurate and stable movement of laparoscopic tools relative to an area of operation and allows manipulation of a greater number of laparoscopic instruments by fewer users than manually operated laparoscopic instruments. This invention also reduces operating staff fatigue by automating more of the control and movement functions necessary in laparoscopic surgery.

SUMMARY OF INVENTION

The disadvantages of the prior art are overcome according to this invention by providing an automated surgical instrument that is adapted to mechanically drive a cannula toward and away from a stationary housing. The housing can be adapted to be held by a hand or can, otherwise, be adapted for mounting on a stationary or movable support. The user manipulates a switch or other control to power a linear motor within the housing that drives a cannula to place its distal end at a predetermined distance from the housing. As such, the cannula may be brought to a certain point within the body through an incision and subsequently driven to an appropriate area upon which an operation is to occur.

A variety of automated tools can be attached to the cannula. These tools include scissors, graspers, trocars, retractors, and electrocautery devices. The cannula can also carry a laparoscope having a camera mount for viewing an operation area. Actuators within the housing are linked to the tools at the distal end of the cannula by means of linkages passing through a lumen in the cannula. Switches for operating the actuators can be located similarly to those for operating the linear drive motors, such as upon the housing, on an associated handle or on a remote control.

BRIEF DESCRIPTION OF THE DRAWINGS

The foregoing and other objects and advantages of the invention will become more clear with reference to the following detailed description of the preferred embodiment and brief description of the drawings in which.

DETAILED DESCRIPTION OF THE PREFERRED EMBODIMENT

Figure 1:
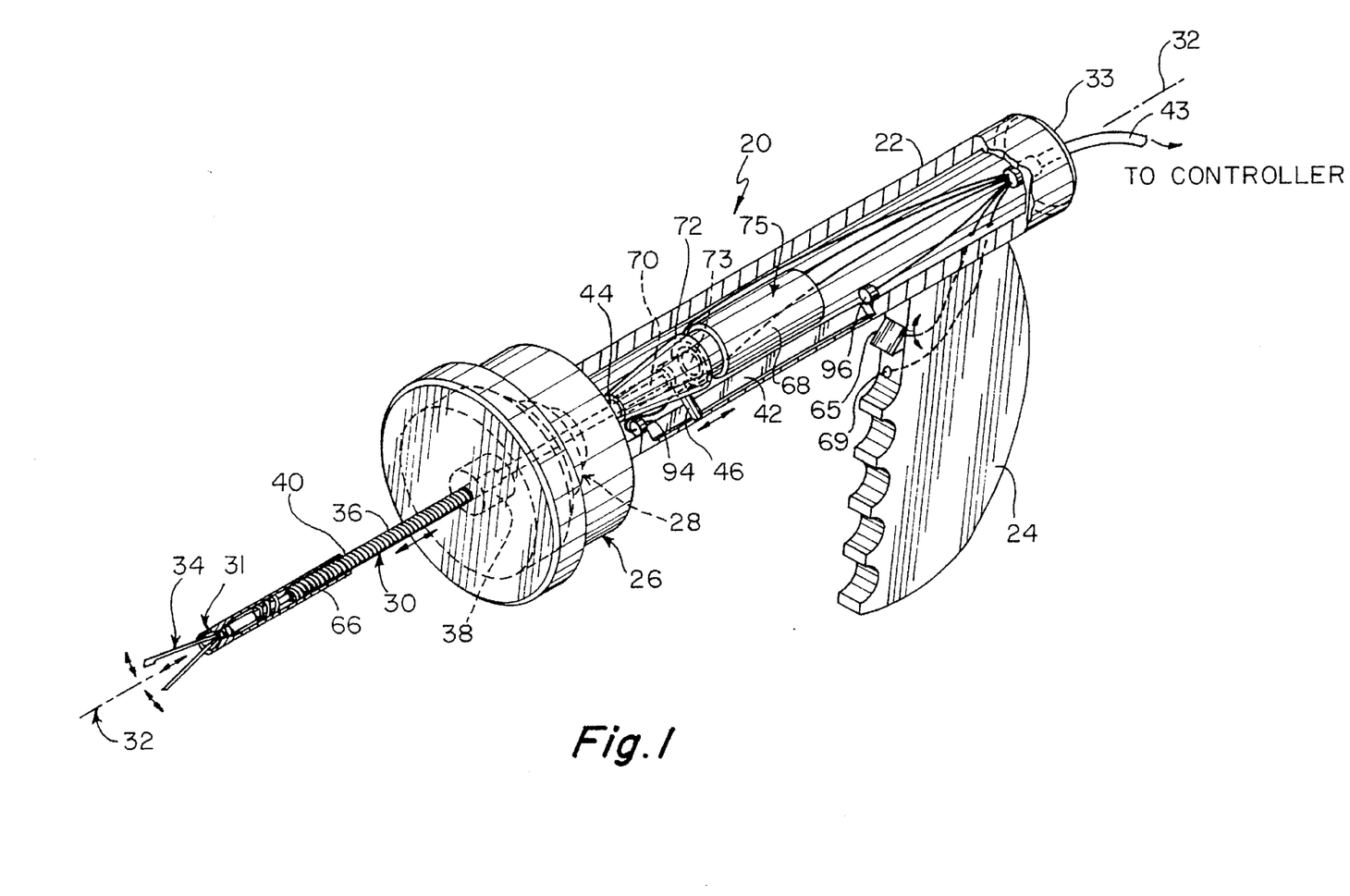
FIG. 1 is an exposed isometric view of an automated surgical instrument according to this invention.

FIG. 1 is an overview of an automated surgical instrument 20 according to this invention. The instrument 20 comprises a housing 22 of plastic, metal or other suitable materials. The housing in this embodiment is substantially cylindrical and elongated. This shape facilitates its mounting in a suitable support or, alternatively, allows it to be held by a grasping hand for manual directing. An optional secondary handle 24 may be attached to the narrowed proximal end of the housing 22 for increased control where manual manipulation or directing is desired. The more distal end of the housing includes an enlarged diameter section 26. The enlarged section 26 houses a linear drive motor 28 for driving an elongated cannula 30 according to this invention. As used herein, "distal" shall mean toward the free end 31 of the cannula 30 and "proximal" shall mean toward the rear end 33 of the housing 22.

The cannula 30 in this embodiment is substantially rigid and structured as a hollow tube having an outer diameter of between 0.2 and 0.4 inches and an inner luminal diameter of between 0.1 and 0.3 inches. The linear drive motor 28 allows the cannula 30 to move relative to its longitudinal axis (the axis in the elongated direction) 32 toward and away from the housing 22. In one embodiment approximately six inches of linear extension of the cannula 30 is contemplated. However, the extension distance of the cannula 30 can be adapted as necessary to perform a particular task. As used herein, the term "cannula" shall refer generally to the elongated tubular portion moves relative to the instrument housing 22.

Figure 2:
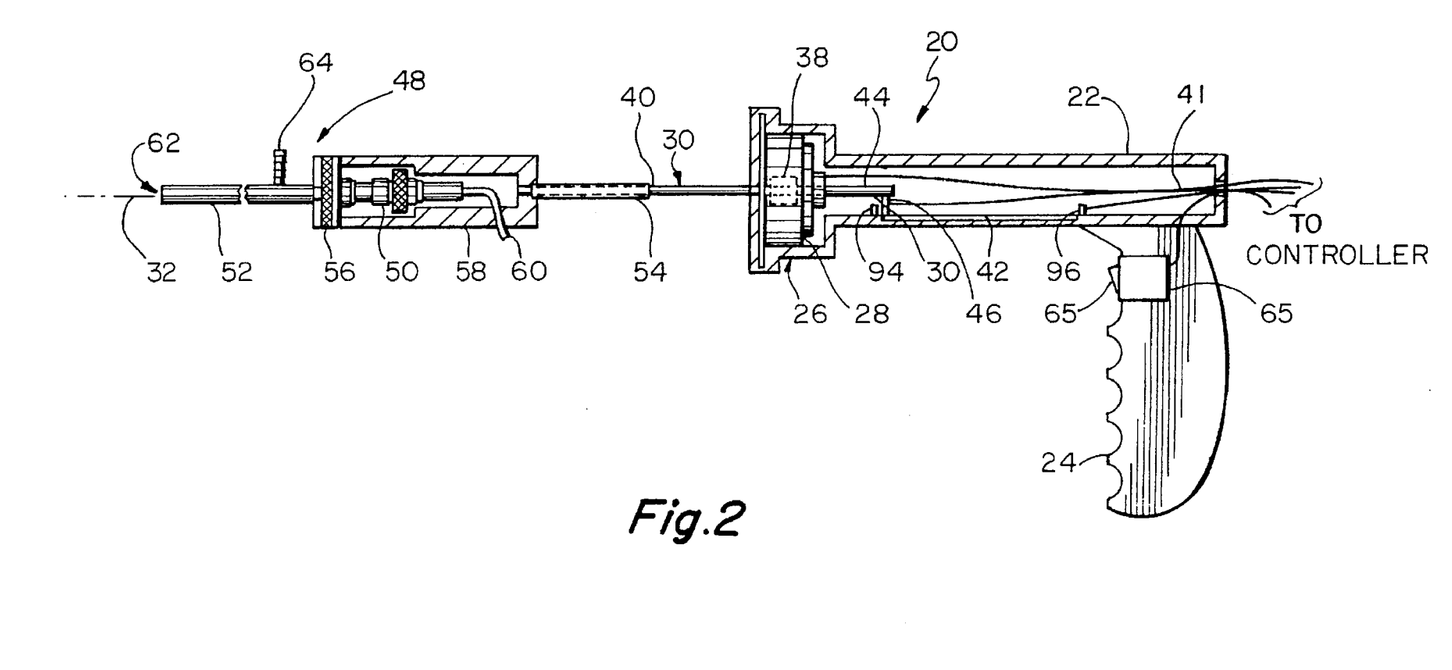
FIG. 2 is a somewhat schematic cross-sectional side view of the automated surgical instrument of FIG. 1 including a laparoscope with a mounted camera according to this invention.
Figure 3:
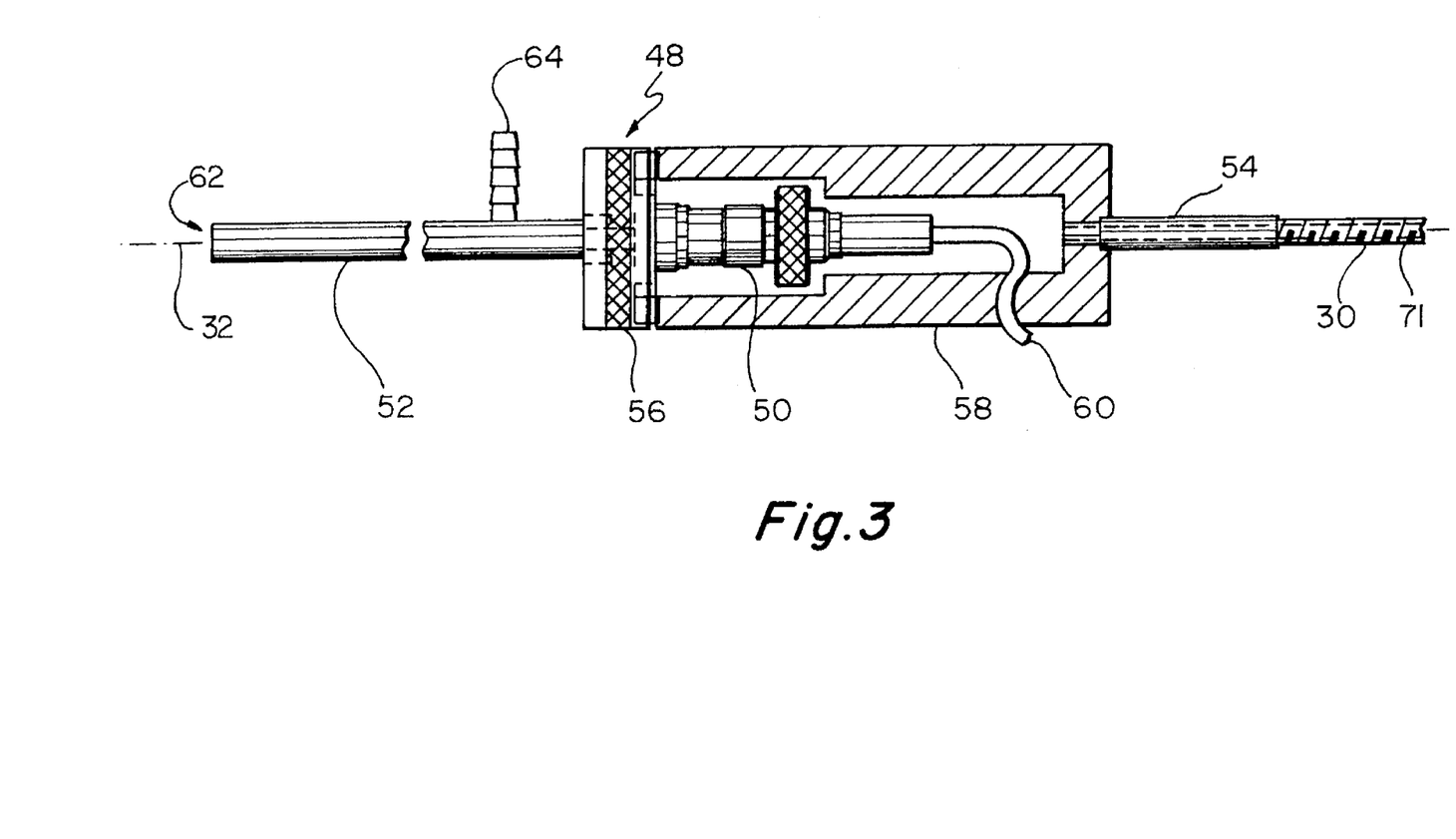
FIG. 3 is a more detailed cross-sectional side view of the laparoscope and camera of FIG. 2.

The cannula 30 is adapted to include a tool 34 at its distal end. The illustrated tool 34 is a pincer-like grasper. Tools will be described further below but, generally, may include a variety of mechanical surgical tools such as scissors and graspers or optical tools such as a laparoscope. FIGS. 2–3 particularly show a laparoscope positioned at the end of the instrument 20 for viewing the interior of a body.

According to this embodiment, the linear drive motor 28 comprises a screw drive. The cannula 30, thus, includes a threaded surface 36 that engages a rotating threaded nut 38 in the motor 28. The motor 28 rotates in each of opposite directions to, respectively, retract and extend the cannula 30. The nut 38 is coaxially positioned within the motor 28 and the cannula 30 can pass through the motor 28 and nut 38 into and out of the housing 22. In this manner, the distal end 40 of the cannula 30 may be accurately positioned relative to the housing 22. To facilitate accurate positioning, the linear motor 28 according to this invention comprises a position-controllable motor such as a stepper motor or a servo motor. Electrical components such as the linear drive motor 28 as used herein are operated by a conventional analog or digital controller (not shown) that receives control inputs from various switches and sensors, both on and remote from the housing 22. The control inputs are translated by the controller into electrical signals to operate the components in a manner to be described further below. Electrical signals in this embodiment are carried through lead wires 41 that can be joined into a control cable 43 exiting the rear 33 of the housing 22 as shown.

The cannula 30 (or an attached proximally positioned member of the cannula) is affixed to a housing channel 42 adjacent the cannula's proximal end 44 by means of a locking pin 46. The pin 46 and channel 42 are sized and arranged so that the cannula 30 may move along the housing 22 in a direction of its longitudinal axis 32, but is prevented from rotating relative to the housing 22 by engagement of the pin 46 with the side walls of the channel 42. In this manner, the cannula 30 does not rotate with the nut 38. Rather, rotation of the nut 38 is translated into linear motion of the cannula 30 along its longitudinal axis 32.

While a screw drive mechanism is depicted, according to a preferred embodiment of this invention, for moving the cannula 30, a variety of other types of linear motors may be utilized to provide extension and retraction of the cannula 30 relative to the housing 22. For example, an electromagnetic linear motor can be utilized to move a magnetically attractive cannula. Similarly, a pneumatic or hydraulic linear actuator can be utilized or a rack and pinion system in which the cannula comprises a rack driven by a set of rotating gears within the motor can be provided.

The instrument 20 according to this invention is designed to carry a variety of accessories upon the distal end 40 of its cannula 30. These accessories are adapted to be inserted through an incision in a patient while the housing 22 and the motor driven (threaded) portion of the cannula 30 remain positioned externally of the patient. FIGS. 2–6 detail variously possible applications of the surgical instrument 20 according to this invention.

FIGS. 2–3 illustrate, in detail, the use of a laparoscope 48 having a camera 50 directed toward its distal end 52 in the surgical instrument 20 according to this invention. The laparoscope 48 is attached by means of a sleeve 54 to the distal end 40 of the lead screw driven cannula 30. The sleeve 54 supports a camera mount 56 that is enclosed in a housing 58 according to this embodiment. The camera 50 includes a lead 60 that projects from the housing 58 and may interconnect with a display device at a remote location (see generally FIG. 7). The distal end 52 of the laparoscope 48 is adapted to be positioned through an incision in the patient to view an area facing the tip 62 of the distal end. Note that the distal end 52 can include a gas port 64 for injecting an inert gas into the cavity of the patient. This allows inflation (or "insufflation") of the affected area for better viewing. The laparoscope 48 can be supported by an external device such as an articulating arm (see generally FIG. 7) or can be handheld.

A secondary handle 24 is provided for gripping and control. This handle is optional, however, and controls can be positioned on the housing or at a remote location. The handle 24 includes a switch 65 having two poles enabling both extension and retraction of the lead screw driven cannula 30. Thus, a surgeon can locate the distal end 62 of the laparoscope 48 within a patient and then finely adjust the positioning of the distal end 62 by moving the lead screw driven cannula 30. The positioning of the distal end 62 in the patient can be quickly altered following an initial insertion by simply toggling the switch 65 to obtain the desired positioning of the distal end 52 of the laparoscope 48.

As noted above, a variety of additional laparoscopic surgical tools can be provided at the distal end 40 of the lead screw driven cannula 30 according to this invention. Referring again to FIG. 1 and now also to FIG. 4, an embodiment of the surgical instrument 20 of this invention adapted to actuate a mechanical laparoscopic surgical tool 34 is shown. The tool 34 is mounted in a sleeve 66 adapted for insertion through an incision. The tool 34 in this example is a form of grasping device that opens and closes upon actuation by the user.

Figure 4:
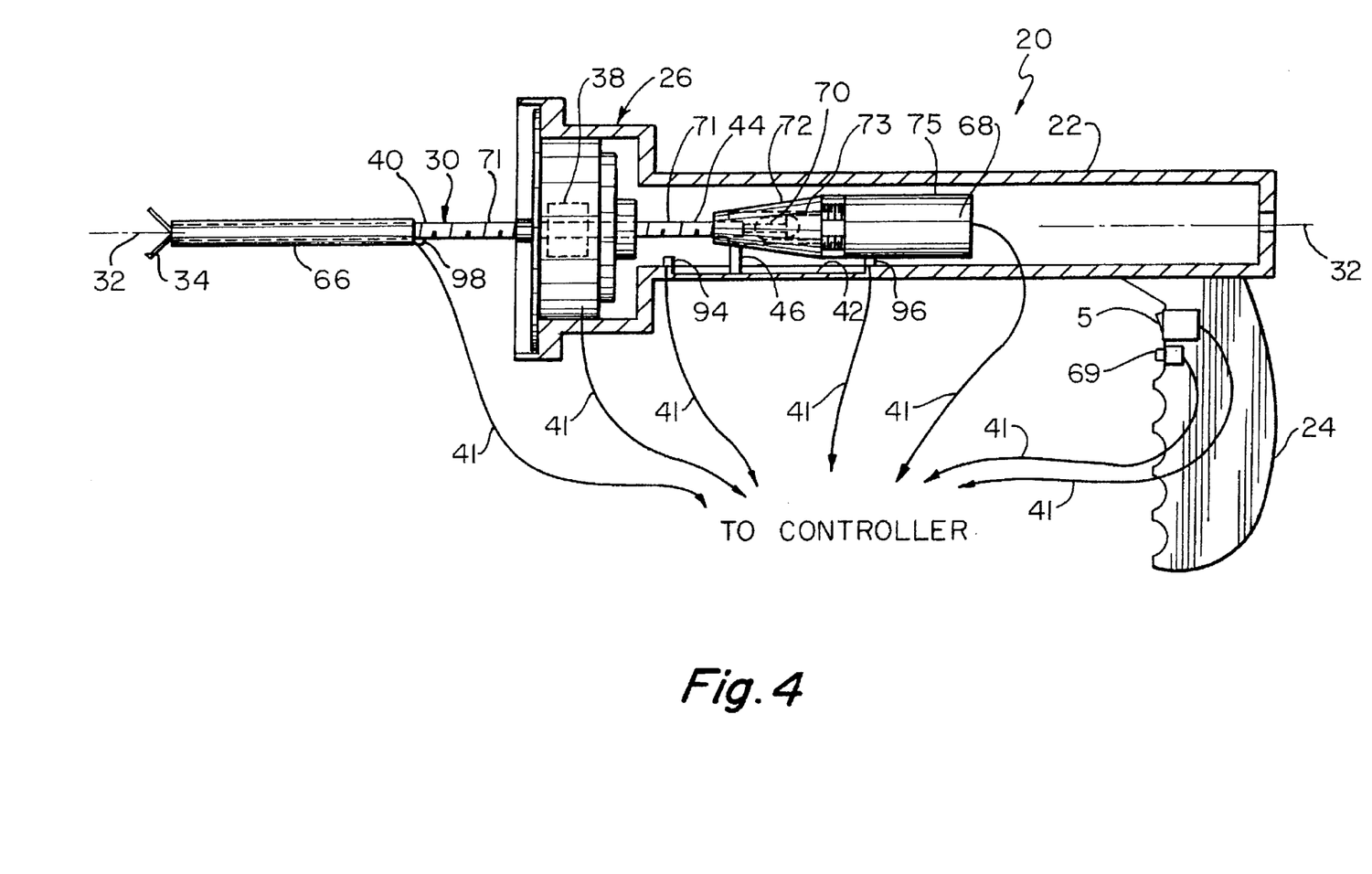
FIG. 4 is a somewhat schematic cross-sectional side view of the automated surgical instrument of FIG. 1 including a tool and actuating mechanism according to this invention.

Actuation of the grasper tool 34 is accomplished by means of an electrically powered linear solenoid actuator 68 positioned within the housing 22 at the proximal end 44 of the lead screw driven cannula 30. The solenoid 68 actuates a linkage 70 that transfers force to operate the tool 34. In this embodiment, the solenoid actuator 68 is fixedly joined to the proximal end 44 of the cannula 30 by a conical sleeve 72 and the linkage 70 passes through the lumen 71 of the cannula 30. A switch 69 on the handle 24 operates the solenoid 68 to move it in a proximally directed direction. The linkage 70 can comprise a tensioned cable or a rigid rod. The conical sleeve 72 of the actuator 68 and the proximal end 44 of the cannula support the locking pin 46 that engages the housing channel 42 to prevent the cannula 30 and actuator 68 from rotating as the drive nut 38 rotates. Both the cannula 30 and the sleeve 66 include the lumen 71 along their respective portion of the longitudinal axis 32 that allows the linkage 70 to pass from the actuator 68 to the tool 34.

The solenoid actuator 68 includes a core 73 capable of movement along the longitudinal axis 32 freely relative to the solenoid outer housing 75. The housing 75 is fixed to the conical sleeve 72 and, hence to the cannula 30. This configuration allows the linkage 70 to move longitudinally while the cannula 30 remains stationary. The operation of some typical tools will now be described below.

Figure 5A:
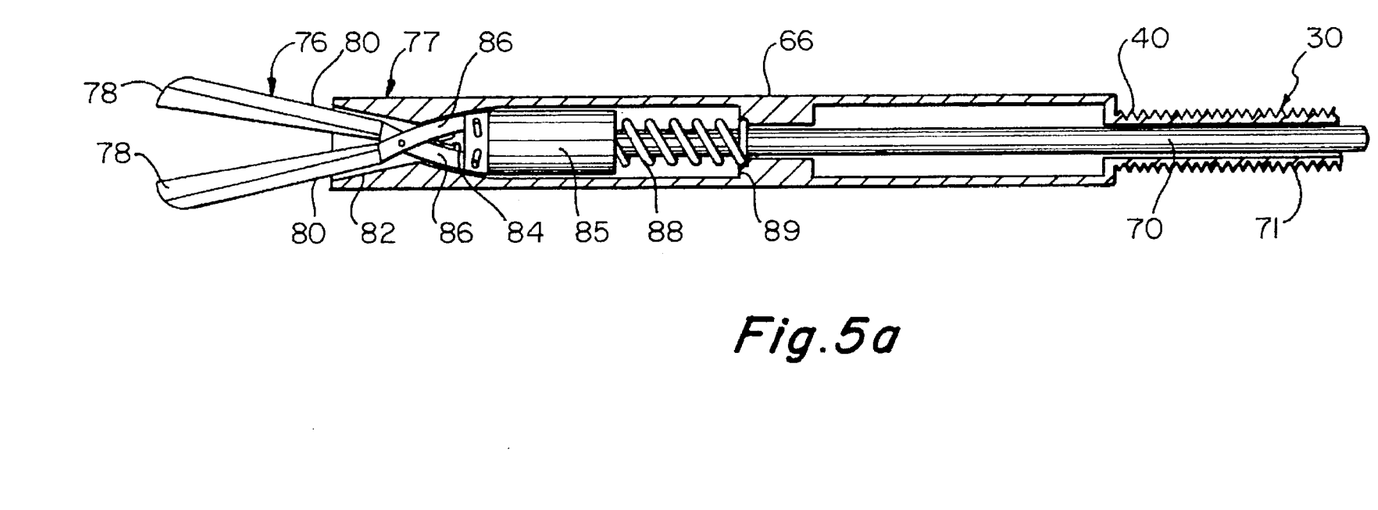
FIGS. 5(a) and 5(b) are cross-sectional side views of a surgical scissor for use with the automated surgical instrument of FIG. 4 in opened and closed positions, respectively.
Figure 5B:
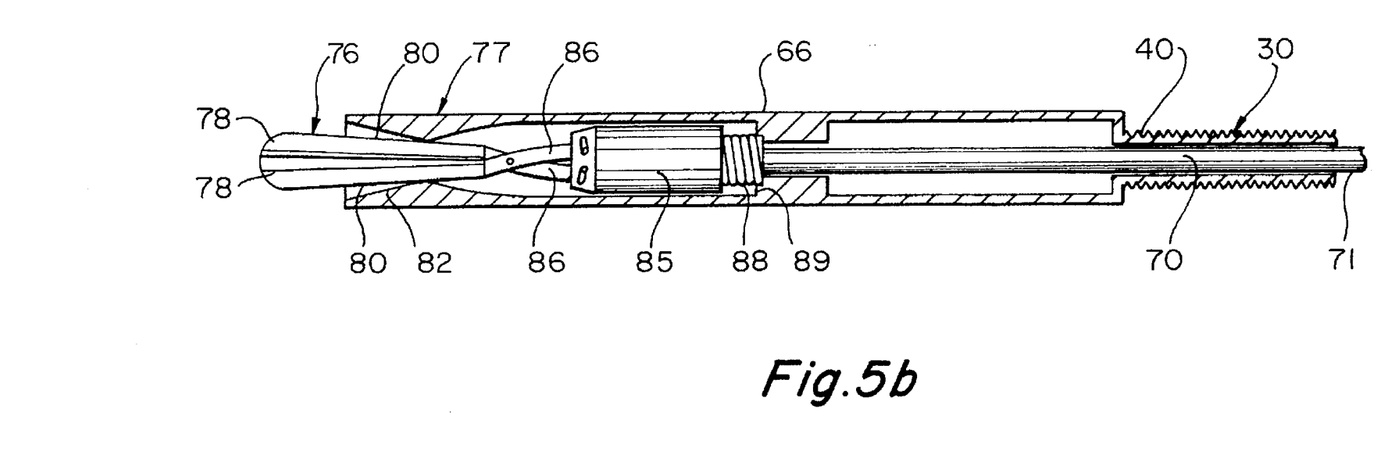

FIGS. 5(a) and 5(b) show a scissor tool 76 positioned within the sleeve 66 at the distal end 77 of the sleeve 66. The scissor 76 includes a pair of sharp blades 78 that, in an open position (FIG. 5(a)), project from the distal end 75 of the sleeve 66. The outer edges 80 of the scissor blades 78 abut a frustoconical inner portion 82 of the sleeve distal end 77. The solenoid actuator 68, when powered, moves the linkage 70 proximally. As the linkage 70 pulls on a block 85 holding the proximal scissor jaws 86, it draws the scissor blades 78 proximally into the sleeve 66. The blades 78 are drawn together as they move proximally by the engagement of the outer edges 80 with the narrowing walls of the frustoconical portion 82. The proximal movement of the blades 78 is opposed by the biasing force of a leaf spring 84 in the proximal jaws 86 and a coil spring 88 between the block 85 and a distal sleeve shoulder 89. The oppositely directed pulling action of the linkage 70, thus, causes the scissor blades 66 to close together as shown in FIG. 5(b).

When the actuator 68 is subsequently depowered, following a cutting stroke, the linkage 70 is free to extend distally under the biasing force of the coil spring 88 and the jaw leaf spring 84, thus allowing the scissor blades 78 to again open for the next cut.

Figure 6A:
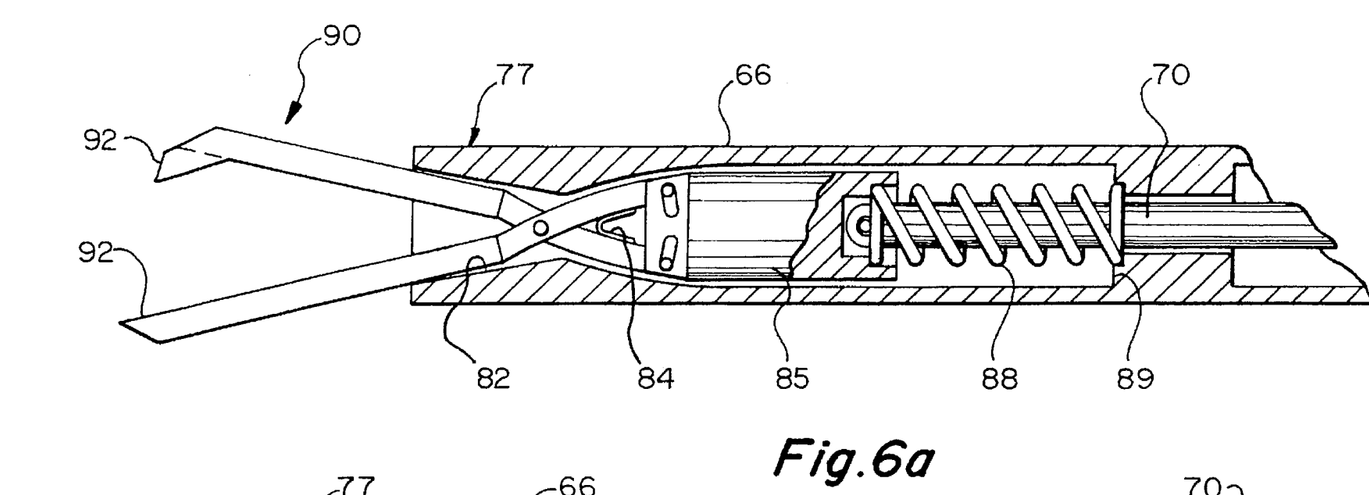
FIGS. 6(a) and 6(b) are cross-sectional side views of a grasping tool for use with the automated surgical instrument of FIG. 4 in opened and closed positions respectively.
Figure 6B:
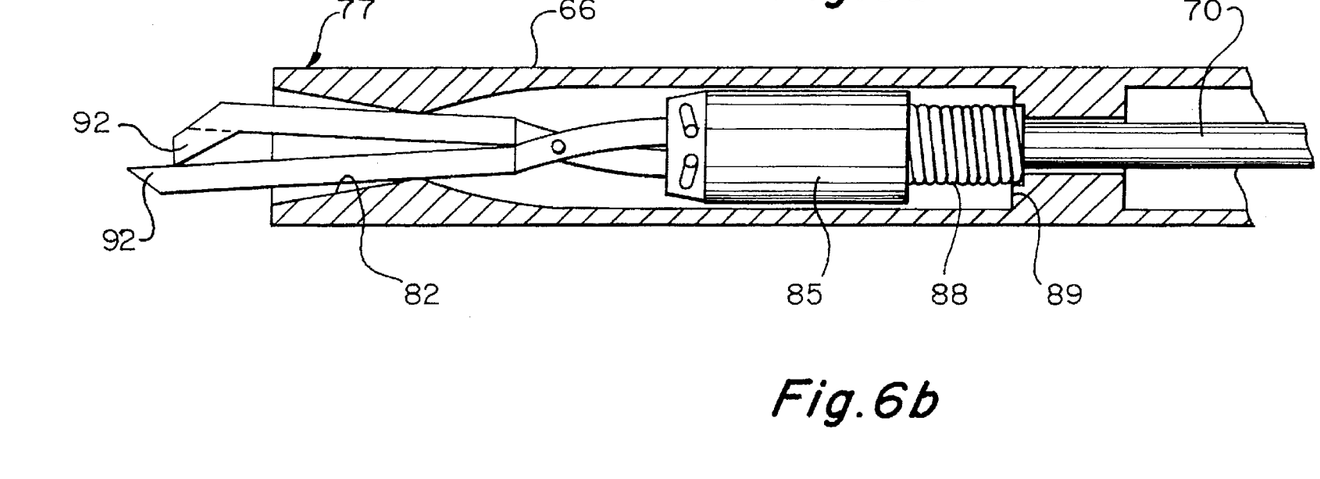

FIGS. 6(a) and 6(b) show a similar mechanism to that described in FIGS. 5(a) and 5(b) for operating a grasper 90 according to this invention. In an opened position as shown in FIG. 6(a), the grasper arms 92 are fully extended from the distal end 77 of the sleeve 66. In a closed, grasping, position, the grasper arms 92 are almost fully retracted into the sleeve 66 with the arms 92 engaging one another and with the coil spring 88 fully compressed.

Various other laparoscopic surgical tools can be attached to the cannula 30 according to this invention. Several of these tools can utilize the solenoid actuator 68 as shown in their operation. Specific examples of surgical tools for use with the instrument 20 include, but are not limited to, trocars, clamps, staplers, retractors, electrocautery devices, vacuum retractors, needles and probes. Other mechanically actuated surgical tools are also contemplated according to this invention. Vacuum, gas and fluid can also be channeled through the lumen 71 of the cannula 30 from the housing 22 or from another location. Similarly, electrocautery wires can be routed through the lumen 71 and used with a specifically designed electorcautery tool or the wires can be incorporated into another laparoscopic surgical tool such as a grasper. The lumen 71 and any tool can also be sized and arranged to allow passage of a fiberoptic or similar optical waveguide for viewing areas adjacent the sleeve's distal end 77. These fiberoptic devices can be mounted in conjunction with one of the above-described tools.

It is contemplated according to this embodiment to control the linear drive motor 28 using a bipolar switch or controller such as a joy stick or toggle switch. The switch can be mounted upon an auxiliary handle as shown in FIGS. 1–2 and 4 (switch 65). Alternatively, the switch can be mounted upon the housing itself and/or at a remote location using, for example, a control box/display console 79 or a foot pedal 83 such as those depicted in FIG. 7.

To further prevent injury to the patient and damage to the instrument, the housing 22 and cannula 30 can be provided with a variety of safety features. FIGS. 1–2 and 4 illustrate a pair of limit switches 94 and 96 that can comprise conventional microswitches according to this embodiment. Each switch 94, 96 is positioned at a location corresponding to one of the two extremes of motion of the cannula 30 relative to the housing. The distally located switch 94 is actuated by the locking pin 46 upon extreme distal extension of the cannula 30 while the proximally located switch 96 is actuated by the pin 46 upon extreme proximal retraction of the cannula 30. Each switch 94 and 96 is interconnected with the controller or control loop (not shown) that operates to disconnect the linear drive motor 28 from its power source when one of the above-described extreme positions relative to the housing 22 is reached by the moving cannula 30. In this manner, the linear drive motor 28 is prevented from over extending the cannula 30 and causing damage to it or to the motor 28 itself. Each switch 94 and 96 only disconnects power directed in the direction of extreme positioning. In other words, once a given limit switch 94 or 96 is tripped, it is still possible to reverse the direction of travel of the cannula 30 to back the cannula 30 away from the extreme and the associated limit switch. When the cannula 30 reaches the opposing limit switch, that switch is then tripped cutting off further power to the linear motor in that direction.

The limit switches 94 and 96 according to this embodiment are particularly adapted to prevent damage to the instrument 20. Additional sensors can also be provided to the cannula 30 or a component connected with the cannula in order to prevent the exertion of undue force upon the patient's internal tissue by the driven cannula 30. FIG. 4 further illustrates a force sensor 98 positioned proximate the sleeve 66 of the surgical tool 34. Other locations along the cannula for the sensor may be utilized according to this invention. The force sensor 98 can comprise a strain gauge, pressure transducer, or a similar device for sensing small increases in the surface strain associated with increased force upon the cannula. The sensor 98 and associated circuitry are calibrated to sense a force in excess of a predetermined value. This value can be set to equal a maximum force that internal tissue can experience without damage. In this manner, the drive motor 28 will stop further advance of the cannula 30 when it begins to bind upon tissue as it is driven into the body. This ensures that the surgeon will not damage internal tissue with the distal end of the tool or laparoscope during extension. Of course, a maximum force adjustment control may be provided to change the maximum force threshold to account for differing operational requirements.

Other forms of proximity sensors may also be provided to the cannula 30 or related components in order to prevent tissue damage. Such sensors can include electrostatic and optical sensors that alert the user that the distal end of the tool or laparoscope has reached a predetermined proximity to tissue. Note that sensor signals can be transferred through the lumen by wires or fiber optic cables from these sensors to the controller (not shown). The sensors can also disable the linear drive motor 28 when the predetermined proximity is reached by the cannula 30.

As an additional feature, the instrument can also include a master power switch located on the handle or at a remote location such as a foot pedal, that allows the user to disable operation of the instrument in the event of a sudden emergency.

A plurality of surgical instruments according to this invention can be utilized and controlled simultaneously during an operative procedure. One such an arrangement is shown generally in FIG. 7. Each instrument (I–IV) is supported by a corresponding articulating arm structure 100 that includes horizontally and vertically oriented pivots 102 and 104, respectively, to allow the instrument to be moved in three dimensions. The arms 100 may be mounted to a post, the ceiling or a comparable support structure 106. The arms include a counter weight or counter force device upon each joint that allow the respective arm to remain fixed in a predetermined spatial position. By predetermined spatial position, it is meant a position suspended relative to an operating area 99 in which the distal end of the cannula may be placed at the area to be operated upon.

Figure 7:
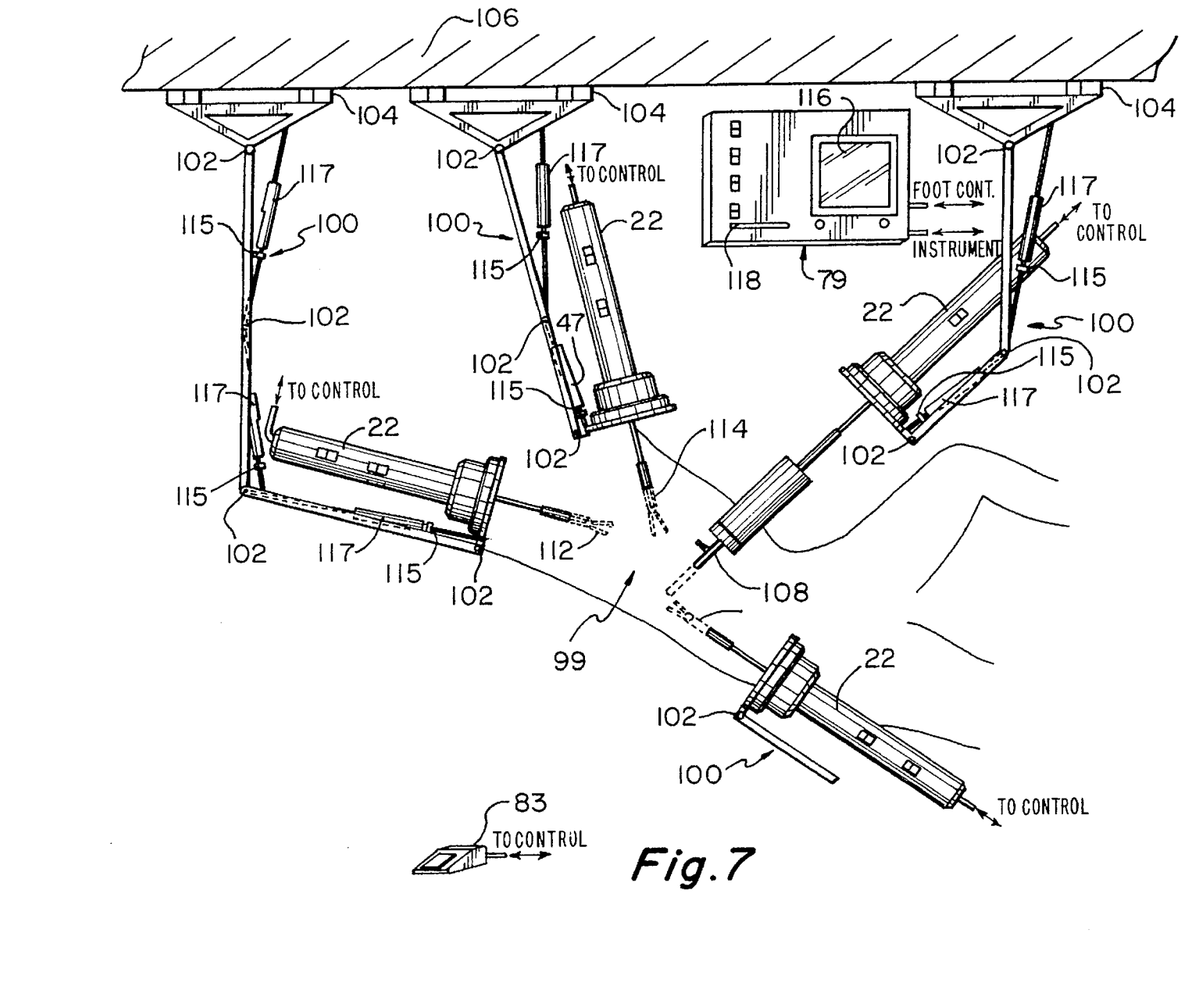
FIG. 7 is a perspective view of a surgical system utilizing a plurality of automated surgical instruments according to this invention.

The arms are each stabilized by counterweighting devices which counteract the weight of the instruments to allow them to remain suspended in whatever position in which the surgeon places them. In this embodiment, the arm is stabilized by air pistons 117 located on arm sections between each horizontal pivot 102. Each arm 100 includes a locking system (lock nuts 115 on the pistons 117 in this embodiment) that allows the arm to be fixed in its desired spatial position. In the configuration of FIG. 7, four separate instruments I–IV, each having a different tool, is utilized including a laparoscope 108, a grasper 110, a scissor 112 and an electrocautery wire/pincer 114.

In air operation using the above-described system, a surgeon first forms an incision at a desired location upon the body and then lowers an instrument into a position with the distal end of its cannula positioned near or within the incision. The arm is then locked in place once the instrument cannula is aligned and angled so that it may pass through the incision into the area to be operated upon. The instrument is then powered to drive the cannula with an appropriate tool at its distal end to the area. Laparoscopic surgical tools are activated as needed to perform, for example, cutting or grasping operations. Tools are extended and retracted as the operation progresses. The laparoscope I is usually inserted first through its own incision to allow viewing, via a display 116, of the progress of the other laparoscopic instruments II–IV, which each enter the operation area 99 through, generally, their own incision.

As noted above, each instrument is operated either by switches located upon the housing or on an associated secondary handle, or upon a remote control/display console 79. Any combination of control locations can be simultaneously used during operation. In this embodiment, the console 79 acts both as a display for the laparoscope I and as a control for each of the laparoscopic instruments II–IV. Each instrument can be controlled separately by accessing the appropriate channel by means of a selector 118 on the console 79. Similarly, a foot control 83 is interconnected with the remote control console to provide optional control capability to the user. The foot control 83 could act to actuate certain selected instruments or could be utilized as an emergency power shut-off switch if necessary. Controls are also provided on the housings 22 of each instrument in this embodiment.

A system utilizing mechanized or automated laparoscopic instruments according to this invention allows for greater control and more reliable adjustment of each of the instruments employed. The automated control of each instrument allows for quicker realignment of its location within the body and more accurate and steady movement from one point to another. Devices may be held in place more steadily. Tool operations, such as cutting and grasping, also prove more predictable and accurate and fatigue of staff members is reduced. The number of required staff members is also reduced.

While there have been shown and described what are at present considered the preferred embodiments of the invention, it will be clear to those skilled in the art that various changes and modifications may be made therein without departing from the scope of the invention as defined by the appended claims. This description, therefore, is meant to be taken only by way of example.

What is claimed is:

1. An automated surgical instrument comprising:
   a housing;
   a substantially rigid tube having a lumen, a distal end projecting from an end of the housing and a proximal end positioned within the housing;
   a drive motor for moving the distal end of the tube toward and away from the housing substantially along a direction of a longitudinal axis of the tube;
   a controller that selectively varies a position of the distal end relative to the housing;
   a surgical tool positioned at the distal end of the tube; and
   an actuator for operating the surgical tool, wherein the actuator includes a linkage positioned through the lumen and connected to the surgical tool, the linkage being interconnected with a drive element that moves the linkage relative to the tube.

2. The automated surgical instrument as set forth in claim 1 wherein the drive motor comprises a screw drive and the tube includes a threaded surface interengaging the screw drive.

3. The automated surgical instrument as set forth in claim 2 wherein the actuator includes a locking lug constructed and arranged to enable the actuator to translate in the housing in substantially a direction of the tube longitudinal axis and to substantially prevent rotation of the actuator and the tube about the tube longitudinal axis.

4. The automated surgical instrument as set forth in claim 2 wherein the screw drive includes a rotary stepper motor.

5. The automated surgical instrument as set forth in claim 4 wherein the screw drive includes a servo motor.

6. The automated surgical instrument as set forth in claim 1 wherein the surgical tool comprises a grasper.

7. The automated surgical instrument as set forth in claim 1 wherein the surgical tool comprises a scissor.

8. The automated surgical instrument as set forth in claim 1 wherein the surgical tool comprises an electrocautery device.

9. The automated surgical instrument as set forth in claim 1 wherein the surgical tool includes a viewing device.

10. The automated surgical instrument as set forth in claim 9 wherein the viewing device comprises a laparoscope having a camera mounted therein.

11. The automated surgical instrument as set forth in claim 10 further comprising a support mechanism that supports the housing in a predetermined spatial position.

12. The automated surgical instrument as set forth in claim 11 wherein the support mechanism comprises an articulating arm.

13. The automated surgical instrument as set forth in claim 12 wherein the articulating arm includes counterbalance means for counteracting the weight of the housing whereby the housing may be maintained at the predetermined spatial position absent external force applied thereto.

14. The automated surgical instrument as set forth in claim 13 wherein the articulating arm includes a locking mechanism to selectively fix the arm in the predetermined spatial position.

15. The automated surgical instrument as set forth in claim 1 wherein the drive element is mounted adjacent the proximal end of the tube and wherein the drive motor moves in conjunction with the tube as the tube moves along the direction of the longitudinal axis of the tube.

16. The automated surgical instrument as set forth in claim 15 wherein the drive element comprises a linear motor.

17. The automated surgical instrument as set forth in claim 16 wherein the linear motor comprises a solenoid.

18. A method for performing minimally invasive surgery comprising:

supporting a housing having a drive motor at a predetermined location remote from a patient;

moving, with the drive motor, a rigid tube having a lumen toward and away from the housing and through and incision in the patient; and operating, at predetermined times, a tool located at a distal end of the tube with a linkage located through the tube that is interconnected with a drive element controlled by a user, the tool being operated to perform a predetermined surgical function on the patient at the location of the incision.

19. The method as set forth in claim 18 wherein the step of supporting includes mounting the housing on an articulating arm that is movable in a plurality of degrees of freedom.

20. The method set forth in claim 18 further comprising providing a second housing having a drive motor at a predetermined location and moving a second rigid tube having a lumen toward and away from the housing and through an incision in the patient.

21. The method as set forth in claim 20 further comprising viewing a predetermined internal area of the patient with a laparoscope having an optical channel that is located at a distal end of the tube of the second housing.

22. The method as set forth in claim 18 wherein the step of moving includes rotating a threaded surface of the drive motor relative to a threaded surface of the tube wherein at least one of the drive motor and the tube is substantially stationary relative to the housing.

23. A method for performing minimally invasive surgery comprising the steps of:

supporting a housing having a drive motor at a predetermined location relative to a patient;

moving a rigid tube having a lumen, and a surgical tube positioned at a distal end thereof, relative to the housing and through an incision in the patient, the step of moving including rotating a threaded surface interconnected with the drive motor relative to an interengaging threaded surface interconnected with the tube, wherein at least one of the drive motor and the tube are substantially free of rotation relative to the housing; and operating the surgical tool within the incision at predetermined times.

24. The method as set forth in claim 23 wherein the step of operating includes operating a laparoscope to view an internal area of the patient through the incision.

25. The method as set forth in claim 23 further comprising providing a movable linkage through the lumen of the tube and operating the surgical tool by moving the linkage.

26. The method as set forth in claim in claim 25 wherein the step of operating includes actuating at least one of a grasper and a scissor.

27. The method as set forth in claim 23, further comprising viewing an interior area of the patient with a laparoscope mounted on the tube.

28. The method as set forth in claim 23, further comprising supporting the housing on an articulating arm that enables movement of the housing in each of a plurality of degrees of freedom.

29. The method as set forth in claim 23 further comprising supporting a second housing having a drive motor at a second predetermined location relative to the patient and moving, with the drive motor, a rigid tube having a lumen toward and away from the housing through an incision in the patient and performing a predetermined surgical function with a tool located at a distal end of the rigid tube.

* * * * *